United States Patent [19]

Ludwig et al.

[11] Patent Number: 5,006,654
[45] Date of Patent: Apr. 9, 1991

[54] METHOD OF PREPARING TRISODIUM 2,4,6-MERCAPTO-S-TRIAZINE NONAHYDRATE

[75] Inventors: Karl Ludwig, Kapellen; Edwin van Raemdonck, Beveren, both of Belgium; Klaus Stützel, Frankfurt, Fed. Rep. of Germany; Marcel Vingerhoets, Brecht, Belgium

[73] Assignee: Degussa Aktiengesellschaft, Frankfurt am Main, Fed. Rep. of Germany

[21] Appl. No.: 355,462

[22] Filed: May 23, 1989

Related U.S. Application Data

[62] Division of Ser. No. 236,842, Aug. 26, 1988, Pat. No. 4,849,517.

[30] Foreign Application Priority Data

Aug. 31, 1987 [DE] Fed. Rep. of Germany ....... 3729029

[51] Int. Cl.$^5$ ............................................. C07D 251/38
[52] U.S. Cl. ...................................................... 544/219
[58] Field of Search ......................................... 544/219

[56] References Cited

PUBLICATIONS

Nakamura et al., Chem. Abstracts; vol. 81; 3972b (1974).

*Primary Examiner*—Mary C. Lee
*Assistant Examiner*—J. Richter
*Attorney, Agent, or Firm*—Cushman, Darby & Cushman

[57] ABSTRACT

The trisodium salt of 2,4,6-trimercapto-s-triazine nonahydrate (TMT-Na$_3$9H$_2$O) is prepared by reacting cyanuric chloride with NaHS and NaOH or with a mixture of NaHS and Na$_2$S and NaOH in an alkaline, aqueous medium.

8 Claims, No Drawings

METHOD OF PREPARING TRISODIUM 2,4,6-MERCAPTO-S-TRIAZINE NONAHYDRATE

This is a division of Application No. 07/236,842, filed Aug. 26, 1988, now U.S. Pat. No. 4,849,517.

The present invention relates to the trisodium salt of 2,4,6-trimercapto-s-triazine nonahydrate (TMT-Na$_3$.9-H$_2$O) and to a method for its preparation.

BACKGROUND OF THE INVENTION

The monosodium salt of 2,4,6-trimercapto-s-triazine has already been by A.W. Hofmann (Ber. 18 2196–2207 1885). He prepared this hygroscopic compound by melting 2,4,6-trimercapto-s-triazine-tri-s-methylester or 2,4,6-trichloro-s-triazine (cyanuric chloride) with sodium sulfide.

A trisodium salt could not be obtained in this manner, as quantitative analysis showed.

Nakamura et al. (C.A. 81, 3972b) describe the preparation of monosodium salt in the form of the trihydrate by reacting NaHS and Na$_2$S with cyanuric chloride in aqueous solution.

A method of fixing heavy metal ions in the earth is disclosed in Published German Patent Application DE-AS 2 240 733 (corresponding to U.S. Pat. No. 3,901,677) in which method, among other things, the aqueous solution of the trisodium salt of 2,4,6-trimercapto-s-triazine is also used. However, a method of preparing this compound is not described.

German Patent Specification DE-OS 3 140 026 relates to a method in which e.g. copper ions are removed from catalysts necessary for the preparation of polyoxyphenylenes with the aid of a 15% aqueous solution of trisodium salt.

Such aqueous solutions are not commercially available.

If these solutions are dewatered, a bright yellow, hygroscopic TMT-Na$_3$ which smells like hydrogen sulfide is obtained. (J. Mangels, thesis, University of Hamburg, 1985).

According to Hofmann, a sodium salt be obtained from the free 2,4,6-trimercapto-s-triazine by means of a reaction with sodium hydroxide solution (loc. cit., p. 2200); however, the free salt was not isolated.

SUMMARY OF THE INVENTION

An object of the present invention is to provide the trisodium salt of 2,4,6-trimercapto-s-triazine nonahydrate.

A further object of the present invention is to provide a method of preparing this compound.

Briefly stated, these objects are achieved by reacting cyanuric chloride in an aqueous medium at temperatures of 20 to 70° C. with NaSH or Na$_2$S or with an NaSH/Na$_2$S mixture, the total amount of sulfur corresponding to three times the molar amount of cyanuric chloride and the pH being held above 7 during the reaction, optionally by the addition of sodium hydroxide solution, and, following the reaction, the mixture obtained being cooled to 0 to 20° C. and the crystallized TMT-Na$_3$.9H$_2$O separated.

The reaction is preferably carried out at 40 to 50° C. and a pH of 9 to 10.

Before the reaction mixture cools off, it is preferable to add still more sodium hydroxide solution to it until the entire amount of sodium hydroxide added is equimolar in amount to the initial concentration of the NaHS in the reaction mixture.

It is advantageous to use a sufficient amount of water so that a 15 to 25% by weight, especially 19 to 21% by weight, TMT-Na$_3$ solution is produced.

The NaHS or the Na$_2$S or the mixture of NaHS and Na$_2$S functions as the sulfur-containing reactant, preferably in a molar ratio of Na$_2$S/NaHS of 0 to 1:4, especially of 1:2 to 1:4.

The separation of the crystallized product takes place after the cooling in a known manner.

Preferably, the solid is centrifuged off and a filter cake is obtained which still contains approximately 5% by weight residual moisture in addition to an amount of water of crystallization of approximately 40% by weight.

The amount of impurities associated with this residual moisture, especially sodium chloride, is so small that TMT-Na$_3$.9H$_2$O has a purity of >97% in relation to the solid content, which was not to be expected. The product is pure white and odorless.

The moisture not present as water of crystallization can be evaporated in a careful manner.

The resulting crystalline material exhibits good flowability and its storage life in air at ambient temperature is surprising. Thus, no change in the properties or in the content (HPLC analysis) could be determined after two months storage.

In contrast thereto, aqueous TMT-Na$_3$ solutions hydrolyze noticeably at room temperature whereas the pure TMT-Na$_3$ is hygroscopic and tends to cake.

The use of the trisodium salt is simplified with the by the new compound prepared in accordance with the present invention since aqueous solutions can now be prepared as required on the spot from the trisodium salt present in storable, crystalline form.

In a preferred embodiment of the method of the invention the filtrate which accumulates during the separation of the crystallized product is processed further It is acidified to pH2-4, preferably with hydrochloric acid. This causes 2,4,6-trismercapto-s-triazine (TMT-H$_3$) to precipitate. This precipitate is separated and added without drying into a sodium hydroxide solution whose concentration is selected in such a manner that a 30–40% by weight TMT-Na$_3$ solution is produced. The trisodium salt is formed. The solution is cooled down to 0 to 20° C., and the salt crystallizes out and is filtered off. The remaining filtrate has a content of approximately 15–20% by weight TMT-Na$_3$, and it can be used as an aqueous medium for further reaction of cyanuric chloride with NaHS and/or Na$_2$S.

It is even simpler to return the TMT-H$_3$ directly into this further reaction stage too, which must then naturally be taken appropriately into account when adding the sodium hydroxide.

This combination of procedures makes it possible to achieve a total yield of at least 90% in relation to cyanuric chloride.

DETAILED DESCRIPTION OF PREFERRED EMBODIMENTS

EXAMPLE 1

72 g 40% by weight aqueous NaSH (1.23 mole) are diluted with 112 ml water. 75 g cyanuric chloride (0.41 mole) and 60 g 50% by weight aqueous NaOH (0.75 mole) are added at 50° C. in such a manner that the pH is held between 9.5 and 10.5 and the temperature at 50°

C. After the addition is over, the mixture is agitated for 1 hour longer at 50° C. and the pH subsequently is adjusted to 12.5 by adding 39 g of 50% by weight aqueous NaOH (0.48 mole). After the mixture has been cooled to 10° C., it is centrifuged. The filter cake weighs 146 g and contains 44.5% by wt. $H_2O$, 54.1 % by wt. TMT-$Na_3$ and 1.3 % by wt. NaCl. The TMT-$Na_3$ content corresponds to a theoretical yield of 79.3 % in relation to the cyanuric chloride added.

The filtrate weighs 312 g and contains 5.2 % by wt. TMT-$Na_3$, which corresponds to a theoretical yield of 16.2 % in relation to the cyanuric chloride added. The filtrate also contains approximately 22.7 % by wt. NaCl and, to a slight extent, hydrolysis products of cyanuric chloride.

The filtrate is acidified with 32 g concentrated hydrochloric acid and TMT-$H_3$ is quantitatively precipitated. The precipitate is separated by filtration and washed with water. The moist filter cake contains 11.7 g TMT-$H_3$ - 100%.

EXAMPLE 2

15 g $Na_2S$ (0.19 mole) and 48.0 g NaHS (0.8 mole) are placed in 133 ml water in a receiver and 65.0 cyanuric chloride (0.35 mole) are added at 40° C. in such a manner that the temperature is maintained. The pH drops to 9 at first and is maintained there by the simultaneous addition of 30 % by wt. aqueous NaOH until all cyanuric chloride has been added. After half an hour postreaction time, the pH is raised to 12.5-13 by adding the remainder of the 115 g (total) of sodium hydroxide solution (0.86 mole). The product workup is performed in the manner described above.

124 g TMT-$Na_3$ filter cake with an NaCl content of 1.4 % by wt., a water content of 44.9 % by wt. and with a TMT-$Na_3$ content of 53.2 % by wt. is obtained, which corresponds to a yield of 77.6% in relation to cyanuric chloride. The 252 g filtrate with 5.1 % by wt. TMT-$Na_3$, which corresponds to a 15.1 % yield in relation to cyanuric chloride, and with 23.5 % by wt. NaCl are treated with 20 g concentrated hydrochloric acid. The TMT-$Na_3$ filter cake is isolated as described previously. It contains 9.3 g TMT-$H_3$ - 100%.

EXAMPLE 3

69 g TMT-$H_3$ filter cake with a TMT-$H_3$ content of 45% by wt. (0.17 mole) and a water content of 55% by wt. are added to 70 g of a 30% by wt. aqueous NaOH (0.52 mole) and the temperature is maintained between 40 and 50° C. by cooling. The clear solution is cooled to 10° C. during which time TMT-$Na_3$ crystallizes which is separated as usual. The centrifuge-moist filter cake weighs 46.0 g and contains 56.5% by wt. TMT-$Na_3$ (0.10 mole) and 43.5% by wt. water.

The filtrate, which weighs 93 g and contains 18% by wt. TMT-$Na_3$ (0.07 mole) is compounded with 56 g NaSH (1 mole) and 136 g water. The reaction with 62.0 cyanuric chloride (0.33 mole) and 80 g 50% by wt. aqueous NaOH (1 mole) and the product recovery were analogous to Example 1. The 139 g filter cake contains 1.1% by wt. NaCl, 44.1% by wt. water and 54.5% by wt. TMT-$Na_3$.

The latter corresponds to a yield of 78.0% TMT-$Na_3$ in relation to the added TMT-$Na_3$ and cyanuric chloride. The filtrate, which weighs 288 g and contains 19.5% by wt. NaCl and 6.1% by wt. TMT-$Na_3$, which corresponds to a yield of 18.1% TMT-$Na_3$ in relation to added TMT-$Na_3$ and cyanuric chloride, is compounded with 37 g concentrated hydrochloric acid and TMT-$H_3$ is isolated.

EXAMPLE 4

33 g TMT-$H_3$ filter cake with an $H_2O$ content of 65% and a TMT-$H_3$ content of 45% by wt. (0.08 mole) are added at 40 to 50° C. in a solution of 36 g NaSH (0.64 mole) and 20.0 g $Na_2S$ (0.26 mole) into 214 g water in portions. Then the reaction is carried out as hitherto described at 50° C. and a pH of 9-10 with 55.0 g cyanuric chloride (0.30 mole) and 71 g 50% by wt. aqueous NaOH (0.90 mole) and prepared as described above. The yield of TMT-$Na_3$ in relation to added cyanuric chloride and TMT-$H_3$ amounts to 69.8% in the filter cake and to 23.2% in the filtrate. The filtrate - 310 g with 6.9% by wt. TMT-$Na_3$, 15% by wt. NaCl is acidified with 32 g concentrated hydrochloric acid and the precipitated TMT-$H_3$ separated. The TMT-$Na_3$ filter cake weighs 119 g and contains 44.7% by wt. $H_2O$, 0.8% by wt. NaCl and 54.2% by wt. TMT-Na3.

What is claimed is:

1. A method of preparing the trisodium salt of 2,4,6-trimercapto-s-triazine nonahydrate (TMT-$Na_3.9H_2O$) which comprises reacting cyanuric chloride in an aqueous medium at a temperature of 20 to 70° C. with a compound selected from the group consisting of NaSH, $Na_2S$ and an NaSH/$Na_2S$ mixture, the total amount of sulfur in said compound corresponding to threefold the molar amount of cyanuric chloride, while maintaining the pH above 7 during the reaction, and, following the reaction, cooling the reaction mixture 0 to 20° C. and separating the crystallized TMT-$Na_3.9H_2O$.

2. A method as set forth in claim 1 including adding sodium hydroxide solution to the reaction mixture.

3. A method as set forth in claim 2 in which sodium hydroxide solution is added to the reaction mixture before it is cooled off, the total amount of sodium hydroxide added to the reaction mixture being an equimolar amount to the initial concentration of NaSH.

4. A method as set forth in any one of claims 1, 2, and 3 in which the amount of water in the reaction mixture is sufficient that a 15 to 25% by wt. TMT-$Na_3$ solution is obtained.

5. A method as set forth in any one of claims 1, 2 and 3 including precipitating 2,4,6-trimercapto-s-triazine (TMT-$H_3$) by acidification of the filtrate which accumulates during the separation of TMT-$Na_3.9H_2O$ to form 2,4,6- trimercapto-s-triazine, and either converting the resultant 2,4,6-trimercapto-s-triazine directly into TMT-$Na_3.9H_2O$ or returning the resultant 2,4,6-trimercapto-s-triazine to the initial reaction mixture.

6. A method as set forth in claim 1 in which the pH during the reaction is in the range 9-10 and the temperature is in the range 40-50° C.

7. A method as set forth in claim 1 in which the compound contains $Na_2S$ and NaSH, and the molar ratio of $Na_2S$ to NHS is in the range 0 to 1:4.

8. A method as set forth in claim 7 in which the molar ratio of $Na_2S$ to NaHS is in the range 1:2 to 1:4.

* * * * *

UNITED STATES PATENT AND TRADEMARK OFFICE
CERTIFICATE OF CORRECTION

PATENT NO. : 5,006,654

DATED : April 9, 1991

INVENTOR(S) : Karl Ludwig Weber, Edwin van Raemdonck, Klaus Stutzel Marcel Vingerhoets It is certified that error appears in the above-identified patent and that said Letters Patent is hereby corrected as shown below:

Please change

"[75] Inventors: Karl Ludwig" to

--[75] Inventors: Karl L. Weber--.

Signed and Sealed this

Seventeenth Day of September, 1991

Attest:

HARRY F. MANBECK, JR.

Attesting Officer

Commissioner of Patents and Trademarks